(12) United States Patent
Muramatsu et al.

(10) Patent No.: US 11,031,748 B2
(45) Date of Patent: Jun. 8, 2021

(54) ILLUMINATION DEVICE, CONTROL DEVICE, AND CONTROL METHOD

(71) Applicant: SONY CORPORATION, Tokyo (JP)

(72) Inventors: Hirotaka Muramatsu, Kanagawa (JP); Akio Furukawa, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/471,198

(22) PCT Filed: Oct. 25, 2017

(86) PCT No.: PCT/JP2017/038530
§ 371 (c)(1),
(2) Date: Jun. 19, 2019

(87) PCT Pub. No.: WO2018/131256
PCT Pub. Date: Jul. 19, 2018

(65) Prior Publication Data
US 2019/0379178 A1 Dec. 12, 2019

(30) Foreign Application Priority Data
Jan. 16, 2017 (JP) .............................. JP2017-004980

(51) Int. Cl.
*H01S 5/40* (2006.01)
*H01S 5/068* (2006.01)
(Continued)

(52) U.S. Cl.
CPC ........ *H01S 5/06804* (2013.01); *F21V 23/003* (2013.01); *F21V 29/503* (2015.01);
(Continued)

(58) Field of Classification Search
CPC ............. H01S 5/02415; H01S 5/02453; H01S 5/4012; H01S 5/4025
See application file for complete search history.

(56) References Cited

U.S. PATENT DOCUMENTS

| | | | |
|---|---|---|---|
| 2004/0179778 A1* | 9/2004 | Hayashi ............... | G05D 23/306 385/34 |
| 2014/0293239 A1* | 10/2014 | Shimizu ................ | G03B 21/16 353/52 |

(Continued)

FOREIGN PATENT DOCUMENTS

| EP | 3064985 A1 | 9/2016 |
|---|---|---|
| JP | 2011-199004 A | 10/2011 |

(Continued)

OTHER PUBLICATIONS

International Search Report and Written Opinion of PCT Application No. PCT/JP2017/038530, dated Dec. 12, 2017, 08 pages of ISRWO.

*Primary Examiner* — Michael Carter
(74) *Attorney, Agent, or Firm* — Chip Law Group

(57) ABSTRACT

To provide an illumination device, a control device, and a control method enabled to perform control to cause output of each of a plurality of light sources to be constant with a more simplified temperature control circuit. There is provided an illumination device including: a plurality of light sources; a plurality of cooling units respectively provided for the light sources and respectively cooling the light sources; and a drive control unit that performs switching of control with respect to each of the light sources on the basis of a comparison between a target temperature of each of the light sources and a measured temperature of each of the light sources or an environment.

11 Claims, 9 Drawing Sheets

(51) Int. Cl.
  *F21V 29/503* (2015.01)
  *F21V 29/54* (2015.01)
  *F21V 23/00* (2015.01)
  *G02B 23/24* (2006.01)
  *H01S 3/042* (2006.01)
  *H01S 5/024* (2006.01)
  *F21Y 115/30* (2016.01)
  *F21Y 113/13* (2016.01)
  *F21V 9/30* (2018.01)
  *H01S 3/0941* (2006.01)
  *H01S 5/343* (2006.01)

(52) U.S. Cl.
  CPC .......... *F21V 29/54* (2015.01); *G02B 23/2469* (2013.01); *H01S 3/042* (2013.01); *H01S 5/02415* (2013.01); *H01S 5/4093* (2013.01); *F21V 9/30* (2018.02); *F21Y 2113/13* (2016.08); *F21Y 2115/30* (2016.08); *H01S 3/0941* (2013.01); *H01S 5/34326* (2013.01); *H01S 5/34333* (2013.01)

(56) References Cited

U.S. PATENT DOCUMENTS

2016/0258611 A1* 9/2016 Takahashi ............ H04N 9/3144
2016/0268771 A1* 9/2016 Ding .................. H04Q 11/0067

FOREIGN PATENT DOCUMENTS

| JP | 2015-056600 A | | 3/2015 |
| JP | 2016-164922 A | | 9/2016 |
| WO | WO2015166728 | * | 11/2015 |

* cited by examiner

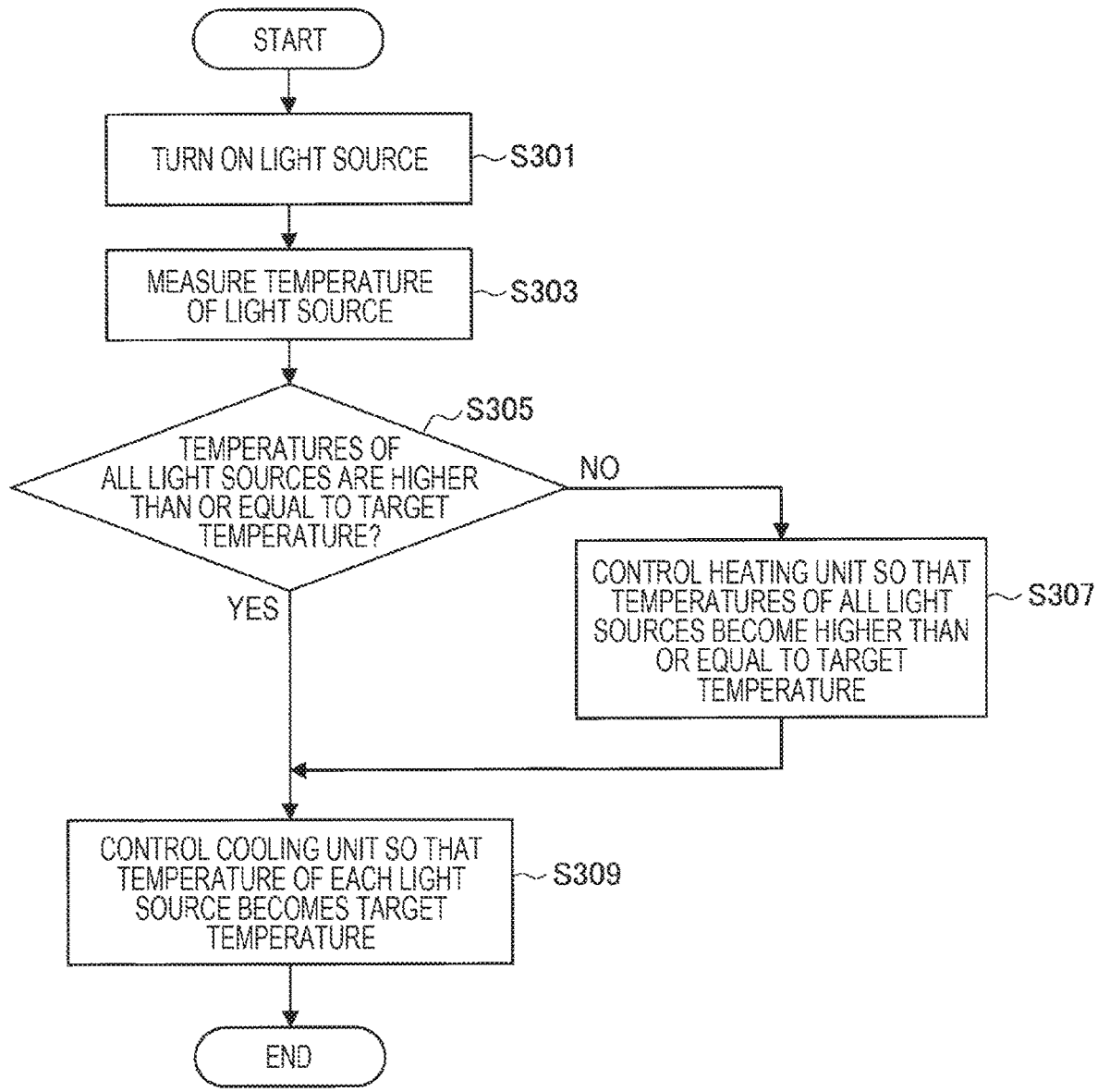

ILLUMINATION DEVICE, CONTROL DEVICE, AND CONTROL METHOD

CROSS REFERENCE TO RELATED APPLICATIONS

This application is a U.S. National Phase of International Patent Application No. PCT/JP2017/038530 filed on Oct. 25, 2017, which claims priority benefit of Japanese Patent Application No. JP 2017-004980 filed in the Japan Patent Office on Jan. 16, 2017. Each of the above-referenced applications is hereby incorporated herein by reference in its entirety.

TECHNICAL FIELD

The present disclosure relates to an illumination device, a control device, and a control method.

BACKGROUND ART

In recent years, in an observation device that observes a surgical field of a patient, such as an endoscope or a microscope, it is common to multiplex lights emitted from a plurality of light sources and use multiplexed light for illumination. For example, as an illumination device such as the endoscope or the microscope, an illumination device has been developed that multiplexes lights from a plurality of laser light sources to emit white light.

However, in the laser light source, a light output characteristic fluctuates depending on a temperature of an element. Furthermore, in the laser light source, in a case where the temperature of the element becomes extremely high, the element rapidly deteriorates. Therefore, in a case where the laser light source is used as the illumination device, it is common that a temperature control function of the laser light source is provided to keep the temperature constant of the element of the laser light source.

For example, in Patent Document 1 below, a light output device is disclosed including a plurality of laser light sources and a plurality of thermoelectric elements respectively provided for the laser light sources, and maintaining a temperature of each of the laser light sources constant by individually controlling heating and cooling by each of the thermoelectric elements.

CITATION LIST

Patent Document

Patent Document 1: Japanese Patent Application Laid-Open No. 2011-199004

SUMMARY OF THE INVENTION

Problems to be Solved by the Invention

However, in the light output device disclosed in Patent Document 1 described above, since it is necessary to individually control heating and cooling in the thermoelectric elements respectively provided for the laser light sources, a control circuit becomes complicated and the number of parts of the control circuit has been increased. In such a case, with the increase in the number of parts of the circuit, a manufacturing cost is increased and reliability is decreased.

Thus, an illumination device, a control device, and a control method have been demanded enabled to perform control to cause light output of each of a plurality of light sources to be constant even in a case where the temperature control circuit is simplified and the number of parts of the circuit is reduced.

Solutions to Problems

According to the present disclosure, there is provided an illumination device including: a plurality of light sources; a plurality of cooling units respectively provided for the light sources and respectively cooling the light sources; and a drive control unit that performs switching of control with respect to each of the light sources on the basis of a comparison between a target temperature of each of the light sources and a measured temperature of each of the light sources or an environment.

Furthermore, according to the present disclosure, there is provided a control device including a drive control unit that performs switching of control with respect to each of a plurality of light sources, the control including at least control of a plurality of cooling units respectively provided for the light sources, on the basis of a comparison between a target temperature of each of the light sources and a measured temperature of each of the light sources or an environment.

Moreover, according to the present disclosure, there is provided a control method including performing switching of control with respect to each of a plurality of light sources, the control including at least control of a plurality of cooling units respectively provided for the light sources, on the basis of a comparison between a target temperature of each of the light sources and a measured temperature of each of the light sources or an environment.

According to the present disclosure, individual heating units respectively controlled for the plurality of light sources are not provided, so that a control circuit can be omitted that controls driving of the heating units.

Effects of the Invention

As described above, according to the present disclosure, control can be performed to cause the light output of each of the plurality of light sources to be constant even with a more simplified temperature control circuit.

Note that, the above-described effect is not necessarily limited, and in addition to the above-described effect, or in place of the above-described effect, any of effects described in the present specification, or other effects that can be grasped from the present specification may be exhibited.

BRIEF DESCRIPTION OF DRAWINGS

FIG. 11 is a flowchart illustrating a flow of operation of a third control example.

MODE FOR CARRYING OUT THE INVENTION

Preferred embodiments of the present disclosure will be described in detail below with reference to the accompanying drawings. Note that, in the present specification and the drawings, constituents having substantially the same functional configuration are denoted by the same reference signs, and redundant explanations will be omitted.

Note that, the description will be made in the following order.
1. Overall configuration of observation device including illumination device
2. Control method of illumination device
2.1. First control example
2.2. Second control example
2.3. Third control example
3. Conclusion <1. Overall Configuration of Observation Device Including Illumination Device>

Figure 1:
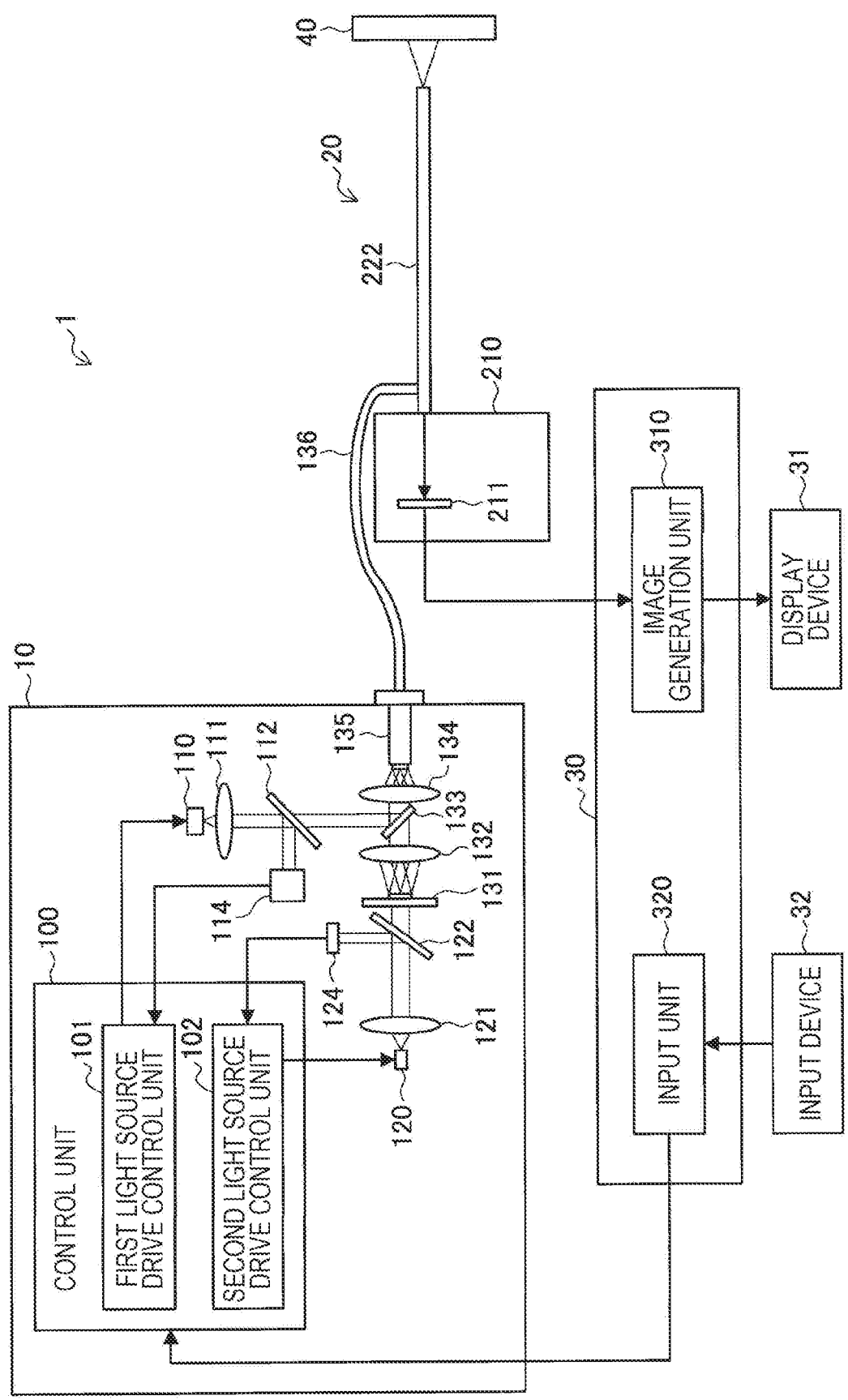
FIG. 1 is an explanatory diagram illustrating an overall configuration of an observation device including an illumination device according to an embodiment of the present disclosure.

First, with reference to FIG. 1, an overall configuration will be described of an observation device including an illumination device according to an embodiment of the present disclosure. FIG. 1 is an explanatory diagram illustrating the overall configuration of an observation device 1 including the illumination device according to the present embodiment.

As illustrated in FIG. 1, the observation device 1 includes a light source unit 10, an endoscope unit 20, an information processing device 30, a display device 31, and an input device 32. Note that the illumination device according to the present embodiment corresponds to the light source unit 10, for example.

(Light Source Unit 10)

The light source unit 10 includes a plurality of light sources, and generates illumination light in which the lights emitted from the plurality of light sources are multiplexed. The illumination light generated by the light source unit 10 is guided from a light guide end 135 to a lens barrel 222 via a light guide 136, and is emitted to an observation target 40 from a tip of the lens barrel 222.

Specifically, the light source unit 10 includes a first light source 110, a first collimating optical system 111, a first semi-transparent mirror 112, a first light detector 114, a control unit 100, a second light source 120, a second collimating optical system 121, a second semi-transparent mirror 122, a second light detector 124, a diffusion member 131, a third collimating optical system 132, a dichroic mirror 133, and a condenser optical system 134.

Light emitted from the first light source 110 passes through the first collimating optical system 111, thereby becoming substantially parallel light and being incident on the dichroic mirror 133. Furthermore, a part of the light emitted from the first light source 110 is demultiplexed by the first semi-transparent mirror 112, and is incident on the first light detector 114.

On the other hand, light emitted from the second light source 120 sequentially passes through the second collimating optical system 121, the diffusion member 131, and the third collimating optical system 132, thereby becoming substantially parallel light and being incident on the dichroic mirror 133. Furthermore, a part of the light emitted from the second light source 120 is demultiplexed by the second semi-transparent mirror 122, and is incident on the second light detector 124.

The dichroic mirror 133 multiplexes the lights emitted from the first light source 110 and the second light source 120. Multiplexed light is incident on the light guide end 135 via the condenser optical system 134, as illumination light.

The first light source 110 is constituted by, for example, a white light source, and emits white light. A type of the white light source constituting the first light source 110 is not particularly limited; however, for example, the first light source 110 may be constituted by a white light emitting diode (LED), a laser excitation phosphor, a xenon lamp, a halogen lamp, or the like, and, specifically, the first light source 110 may be constituted by a so-called phosphor type white LED using a phosphor excited by a blue LED.

The first collimating optical system 111 converts the white light emitted from the first light source 110 into a parallel light flux, and causes the parallel light flux to be incident on the dichroic mirror 133 from a direction different from a direction of light passing through the third collimating optical system 132 (for example, a direction in which the optical axes are substantially orthogonal to each other). Note that, the light having passed through the first collimating optical system 111 does not have to be a perfect parallel light ray, and may be divergent light in a state close to a parallel light ray.

The first semi-transparent mirror 112 is provided between the first light source 110 and the dichroic mirror 133, for example, and demultiplexes a part of the light emitted from the first light source 110. Demultiplexed light is incident on the first light detector 114. Note that, the first semi-transparent mirror 112 is an example of a demultiplexing member, and another demultiplexing member may be used instead of the first semi-transparent mirror 112.

The first light detector 114 detects an intensity of the light emitted from the first light source 110, and outputs the detected intensity of the light to a first light source drive control unit 101. As a result, the first light source drive control unit 101 can control the intensity of the light emitted from the first light source 110 on the basis of the intensity of the light detected, for example. The first light detector 114 may be constituted by a known light detector, for example, a photodiode, a color sensor, or the like.

The second light source 120 includes at least one or more laser light sources that emit light in a predetermined wavelength band. For example, the second light source 120 may include a red laser light source that emits a laser light in the red band (for example, a laser light having a center wavelength of about 638 nm), a green laser light source that emits a laser light in the green band (for example, a laser light having a center wavelength of about 532 nm), and a blue laser light source that emits laser light in the blue band (for example, laser light having a center wavelength of about 450 nm).

The second light source 120 includes the red laser light source, the green laser light source, and the blue laser light source that emit lights in the respective wavelength bands corresponding to the three primary colors of light, whereby the laser lights emitted from the respective laser light sources are multiplexed and white light can be generated. Furthermore, the second light source 120 can also adjust a color temperature of the multiplexed white light by appropriately adjusting a ratio of amounts of light of the red laser light source, the green laser light source, and the blue laser light source.

Note that, the red laser light source, the green laser light source, and the blue laser light source may be constituted by various known laser light sources such as a semiconductor laser or a solid laser. Furthermore, for the red laser light source, the green laser light source, and the blue laser light source, the center wavelength may be controlled by combination with a wavelength conversion mechanism.

Note that, the laser light source is a light source whose light output characteristic changes depending on the temperature. Furthermore, the temperature of the laser light source rises due to oscillation of the laser light, and in a case where the temperature of the laser light source excessively rises, the life of the laser light source may be shortened. Therefore, the laser light source is provided with a cooling unit for suppressing a rise in the temperature of the laser light source. A specific method of temperature control for these laser light sources will be described later.

The second collimating optical system 121 converts the light emitted from the second light source 120 (in other words, the light in which the lights of the respective laser light sources are multiplexed) into a parallel light flux. The second collimating optical system 121 converts the light to be incident on the diffusion member 131 provided in the subsequent stage into the parallel light flux, thereby facilitating control of a diffusion state of the light in the diffusion member 131. Note that, the light having passed through the second collimating optical system 121 does not have to be a perfect parallel light ray, and may be divergent light in a state close to a parallel light ray.

The second semi-transparent mirror 122 is provided between the second collimating optical system 121 and the diffusion member 131, for example, and demultiplexes a part of the light emitted from the second light source 120. Note that, demultiplexed light is incident on the second light detector 124. Note that, the second semi-transparent mirror 122 is an example of a demultiplexing member, and another demultiplexing member may be used instead of the second semi-transparent mirror 122.

The second light detector 124 detects an intensity of the light emitted from the second light source 120, and outputs the detected intensity of the light to a second light source drive control unit 102. As a result, the second light source drive control unit 102 can control the intensity of the light emitted from the second light source 120 on the basis of the intensity of the light detected, for example. The second light detector 124 may be constituted by a known light detector, for example, a photodiode, a color sensor, or the like.

The diffusion member 131 is provided in a near range of a focal position of the second collimating optical system 121 (for example, in a range of about 10% of a focal length in the front-to-back direction from the focal position), and diffuses light emitted from the second collimating optical system 121. As a result, a light emitting end in the diffusion member 131 can be regarded as a secondary light source. Since there may be variations in the divergence angle for each of the multiplexed light in the light in which the lights emitted from the plurality of laser light sources are multiplexed, the divergence angle of the emitted light is uniformized by conversion to the secondary light source through the diffusion member 131.

A size of the secondary light source generated by the diffusion member 131 can be controlled by the focal length of the second collimating optical system 121. Furthermore, a numerical aperture (NA) of emitted light of the secondary light source generated by the diffusion member 131 can be controlled by a diffusion angle of the diffusion member 131. Therefore, in the diffusion member 131, it is possible to independently control both a size of a condensing spot and an incident NA at the time of coupling to the light guide end 135.

A type of the diffusion member 131 is not particularly limited, and various known diffusion elements can be used. For example, the diffusion member 131 may be a frosted ground glass, an opal diffusion plate in which a light diffusion substance is dispersed in glass, a holographic diffusion plate, or the like. Note that, in the holographic diffusion plate, it is also possible to arbitrarily set the diffusion angle of the emitted light depending on a holographic pattern applied on the substrate.

The third collimating optical system 132 converts the light from the diffusion member 131 (in other words, the light from the secondary light source) into a parallel light flux, and causes the parallel light flux to be incident on the dichroic mirror 133. Note that, the light having passed through the third collimating optical system 132 does not have to be a perfect parallel light ray, and may be divergent light in a state close to a parallel light ray.

The dichroic mirror 133 multiplexes the light emitted from the first light source 110 and the light emitted from the second light source 120 that are incident from directions in which the optical axes are substantially orthogonal to each other.

For example, the dichroic mirror 133 may be designed to transmit only light in a wavelength band corresponding to the light from the second light source 120, and reflect light in other wavelength bands. In such a case, for example, in the dichroic mirror 133, the light emitted from the second light source 120 is transmitted through the dichroic mirror 133, and is incident on the condenser optical system 134. Furthermore, regarding the light emitted from the first light source 110, only a component other than the wavelength band of the light emitted from the second light source 120 is reflected by the dichroic mirror 115, and is incident on the condenser optical system 134. As a result, the dichroic mirror 133 can multiplex the light emitted from the first light source 110 and the light emitted from the second light source 120.

Note that, the dichroic mirror 133 is an example of a multiplexing member that multiplexes the lights respectively emitted from the first light source 110 and the second light source 120, and another multiplexing member can be used. For example, in the light source unit 10, a plurality of lights may be multiplexed in wavelength by using a dichroic prism as a multiplexing member, the plurality of lights may be multiplexed in polarization by using a polarizing beam splitter as the multiplexing member, or the plurality of lights may be multiplexed in amplitude by using a beam splitter as the multiplexing member.

The condenser optical system 134 is constituted by, for example, a condenser lens, and images the light multiplexed by the dichroic mirror 133 on the light guide end 135 with a predetermined paraxial lateral magnification.

The light guide 136 guides the light emitted from the light source unit 10 to the lens barrel 222. The light guide 136 may be constituted by, for example, an optical fiber. However, a type of the optical fiber constituting the light guide 136 is not particularly limited, and it is possible to use a known multimode optical fiber (for example, step index multimode fiber, or the like). Furthermore, a core diameter of the optical fiber is not particularly limited, and for example, it is sufficient that the core diameter of the optical fiber is about 1 mm.

In the light source unit 10, an imaging magnification by the third collimating optical system 132 and the condenser optical system 134 can be set by (focal length of the condenser optical system 134)/(focal length of the third collimating optical system 132). The imaging magnification by the third collimating optical system 132 and the condenser optical system 134 is set so that the size and divergence angle of the secondary light source match the core diameter and incident NA of the light guide 136.

Furthermore, an imaging magnification by the first collimating optical system 111 and the condenser optical system 134 can be set by (focal length of the condenser optical system 134)/(focal length of the first collimating optical system 111). The imaging magnification by the first collimating optical system 111 and the condenser optical system 134 is set so that the light from the first light source 110 matches the core diameter and incident NA of the light guide 136 and is coupled to the light guide end 135 with high efficiency.

The control unit 100 is a control circuit that controls each component of the light source unit 10. Specifically, the control unit 100 includes the first light source drive control unit 101 that controls each component of the first light source 110, and the second light source drive control unit 102 that controls each component of the second light source 120. The control unit 100 is constituted by, for example, a processor such as a central processing unit (CPU), a micro processing unit (MPU), or a digital signal pocessor (DSP), and these processors execute arithmetic processing in accordance with a predetermined program to implement various functions.

Specifically, the first light source drive control unit 101 controls light emission output of the first light source 110. For example, the first light source drive control unit 101 may control the light emission output of the first light source 110 by changing a drive current of the first light source 110 (for example, a white LED light source).

Furthermore, the second light source drive control unit 102 controls light emission output of the second light source 120. For example, the second light source drive control unit 102 may control the light emission output of the second light source 120 by changing a drive current of the second light source 120 (for example, a plurality of laser light sources corresponding to respective colors of RGB).

Here, in a case where the second light source 120 is constituted by at least one or more laser light sources, the second light source drive control unit 102 may perform control to keep the temperatures of the laser light sources constant to maintain oscillation wavelengths and light output characteristics of the laser light sources constant. For example, the second light source drive control unit 102 may perform control to keep the temperatures constant of the laser light sources constituting the second light source 120 by controlling driving of a cooling element on the basis of temperature information of the second light source 120 measured by a temperature measurement element. Note that, details will be described later of the temperature control of such a light source.

(Endoscope Unit 20)

The endoscope unit 20 includes the lens barrel 222 and an imaging unit 210.

In the lens barrel 222, the light guide 136 is extended to a tip portion, and the illumination light emitted from the light source unit 10 is guided to the observation target 40. Furthermore, the lens barrel 222 guides the light reflected by the observation target 40 to the imaging unit 210. The lens barrel 222 may be formed in a substantially cylindrical shape having rigidity, or may be formed in a tubular shape having flexibility.

The imaging unit 210 includes an imaging element 211 enabled to acquire a color image, and performs photoelectric conversion of the light from the observation target 40 by the imaging element 211 to convert the light into an electric signal. Note that, the electric signal subjected to the photoelectric conversion by the imaging element 211 is output to the information processing device 30. The imaging element 211 may be any of various known imaging elements, such as a charge coupled device (CCD) image sensor, or a complementary metal oxide semiconductor (CMOS) image sensor.

(Information Processing Device 30)

The information processing device 30 generates a captured image (observation image) of the observation target 40 on the basis of the electric signal subjected to photoelectric conversion by the imaging unit 210. Specifically, the information processing device 30 includes an image generation unit 310 and an input unit 320. Note that, the information processing device 30 may be a personal computer or the like mounting a central processing unit (CPU), a read only memory (ROM), a random access memory (RAM), and the like.

The image generation unit 310 generates an observation image of the observation target 40 on the basis of the electric signal from the imaging element 211. The observation image generated by the image generation unit 310 is output to the display device 31, for example, thereby being visually recognized by a user.

The input unit 320 generates an input signal on the basis of an input to the input device 32 by the user, and outputs the input signal to the control unit 100 or the like. The input unit 320 may output an input signal for changing control with respect to the first light source 110 or the second light source 120 to the first light source drive control unit 101 or the second light source drive control unit 102, for example.

(Display Device 31)

The display device 31 displays the observation image generated by the image generation unit 310 of the information processing device 30. The display device 31 may be, for example, a cathode ray tube (CRT) display device, a liquid crystal display device, a plasma display device, an organic EL display device, or the like.

(Input Device 32)

The input device 32 is an input interface that accepts input operation by the user. The input device 32 is an input device to which information is input, for example, a mouse, a keyboard, a touch panel, a button, a microphone, a switch, a lever, and the like. The user controls the observation device 1 by operating the input device 32, and can change a magnification, amount of light, and the like of the observation image, for example.

The observation device 1 having the above configuration can be used as, for example, an endoscope device and a microscope device.

<2. Control Method of Illumination Device>

Next, with reference to FIGS. 2 to 11, the control method will be described of the illumination device according to the present embodiment, by dividing the method into first to third control methods. Note that, in the following, description will be made, as an example of the illumination device according to the present embodiment, by using the second light source 120 including the plurality of laser light sources corresponding to the respective colors of RGB (red, green, blue), and the second light source drive control unit 102 that controls the second light source 120. Furthermore, for simplicity, the second light source 120 is also referred to as a light source, and the second light source drive control unit 102 is also referred to as a drive control unit.

(2.1. First Control Method)

Figure 2:
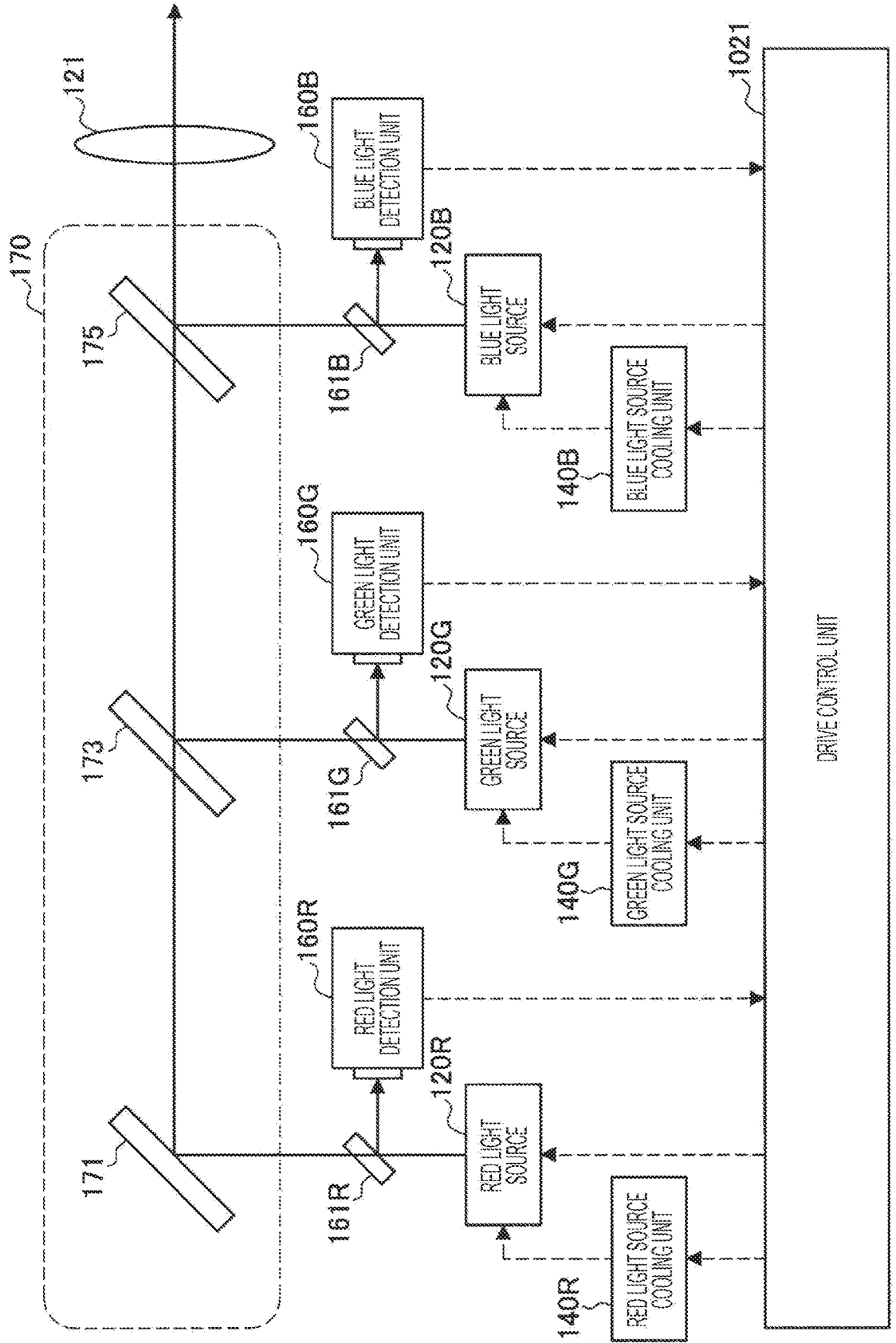
FIG. 2 is a block diagram illustrating each component of an illumination device according to a first control method.

First, with reference to FIGS. 2 to 6, a first control method of the illumination device will be described. FIG. 2 is a block diagram illustrating each component of an illumination device according to the first control method.

In the illumination device according to the first control method, each laser light source includes the cooling unit, but does not include a heating unit. Therefore, in the illumination device according to the first control method, the number of parts can be reduced of the control circuit that controls the heating unit. However, due to the fact that each laser light source does not include the heating unit, in a case where the temperature of each laser light source of the illumination device is lower than a target temperature for stabilization, the amount of light of each laser light source may fluctuate. In the first control method, a control method is provided for keeping the amount of light of the illumination device constant even in such a case.

As illustrated in FIG. 2, the illumination device according to the first control method includes: a red light source 120R, a green light source 120G, and a blue light source 120B (collectively, also referred to as the light source 120); a red light source cooling unit 140R, a green light source cooling unit 140G, and a blue light source cooling unit 140B (collectively, also referred to as a cooling unit 140); light samplers 161R, 161G, and 161B (collectively, also referred to as a light sampler 161); a red light detection unit 160R, a green light detection unit 160G, and a blue light detection unit 160B (collectively, also referred to as a light detection unit 160); a multiplexing module including a mirror 171, and dichroic mirrors 173 and 175; and a drive control unit 1021.

The red light source 120R is, for example, a laser light source that emits light in a wavelength range of 630 nm to 645 nm, and may be constituted by a semiconductor laser such as an AlGaInP quantum well structure laser diode. The green light source 120G is, for example, a laser light source that emits light in a wavelength range of 510 nm to 540 nm, and may be constituted by a solid laser excited by a semiconductor laser, or may be constituted by attaching a wavelength conversion filter to a semiconductor laser emitting light in a different wavelength range. The blue light source 120B is, for example, a laser light source that emits light in a wavelength range of 435 nm to 465 nm, and may be constituted by a semiconductor laser such as a GaInN quantum well structure laser diode.

Note that, the above-described red light source 120R, green light source 120G, and blue light source 120B are merely examples, and the plurality of light sources included in the illumination device according to the present embodiment is not limited to the above. For example, the illumination device according to the present embodiment may include a light source corresponding to a color other than RGB, a plurality of light sources of one color, a plurality of light sources of two colors, or a plurality of light sources of four or more colors. Furthermore, the plurality of light sources may be white light sources.

In the laser light source, unlike a lamp light source such as the xenon lamp or the halogen lamp, the amount of light of the emitted light can be adjusted by control of the drive current or drive voltage applied to the laser light source. However, since the light output characteristic of the laser light source may fluctuate depending on the temperature, even if the applied current is constant, the amount of light, oscillation wavelength, and the like of the light emitted may fluctuate depending on the temperature. Therefore, in the illumination device according to the present embodiment, the red light source cooling unit 140R, the green light source cooling unit 140G, and the blue light source cooling unit 140B are respectively provided for the light sources 120 to suppress the temperature rises of the laser light sources. Note that, examples of a fluctuation factor of the temperature of the laser light source includes heat generation by driving of the laser light source, an environmental temperature of a space where the illumination device is installed, and the like.

The red light source cooling unit 140R, the green light source cooling unit 140G, and the blue light source cooling unit 140B cool the respective light sources 120. Specifically, the red light source cooling unit 140R, the green light source cooling unit 140G, and the blue light source cooling unit 140B are respectively provided for the red light source 120R, the green light source 120G, and the blue light source 120B, and respectively cool the red light source 120R, the green light source 120G, and the blue light source 120B. The cooling unit 140 may be, for example, a thermoelectric element such as a Peltier element.

Note that, the Peltier element is an element that executes both functions of cooling and heating by reverse of the polarity of the flowing current; however, in a case where the Peltier element is used for the cooling unit 140, the Peltier element is configured to execute only the function of cooling the light source 120. Specifically, in the Peltier element constituting the cooling unit 140, only a circuit is provided for supplying a current in a direction to cool the light source 120, and a circuit is not provided for supplying current in a direction to heat the light source 120.

The light samplers 161R, 161G, and 161B each demultiplex a part of the light emitted from the light source 120. Specifically, the light samplers 161R, 161G, and 161B are respectively provided between the red light source 120R, the green light source 120G, and the blue light source 120B, and the mirror 171, and the dichroic mirrors 173 and 175, and each demultiplex a part of the emitted light from a corresponding one of the red light source 120R, the green light source 120G, and the blue light source 120B. The emitted lights demultiplexed by the light samplers 161R, 161G, and 161B are respectively incident on the red light detection unit 160R, the green light detection unit 160G, and the blue light detection unit 160B. As a result, the red light detection unit 160R, the green light detection unit 160G, and the blue light detection unit 160B can respectively detect the amounts of light of red light, green light, and blue light.

The red light detection unit 160R, the green light detection unit 160G, and the blue light detection unit 160B each detect the amount of light emitted from the light source 120. Specifically, the red light detection unit 160R, the green light detection unit 160G, and the blue light detection unit 160B respectively detect the amounts of light emitted from the red light source 120R, the green light source 120G, and the blue light source 120B. Furthermore, the light detection unit 160 converts the amount of light of the light received from each of the light sources 120 into an electric signal, and outputs the electric signal to the drive control unit 1021. For example, the light detection unit 160 may be constituted by a photodiode, or a color sensor including a color filter for spectroscopy.

A multiplexing module 170 multiplexes the red light, the green light, and the blue light respectively emitted from the red light source 120R, the green light source 120G, and the blue light source 120B, and generates illumination light to be emitted to the observation target 40. Specifically, the multiplexing module 170 includes the mirror 171, and the dichroic mirrors 173 and 175. Note that, each of the dichroic mirrors 173 and 175 is a mirror that reflects light of a specific wavelength and transmits light of a wavelength other than the reflected light.

In the multiplexing module 170, the mirror 171 reflects the red light emitted from the red light source 120R and causes the reflected red light to be incident on the dichroic mirror 173. Furthermore, the dichroic mirror 173 reflects the green light emitted from the green light source 120G, thereby causing the reflected green light to be incident on the dichroic mirror 175, and transmits the red light incident from a direction orthogonal to an incident direction of the green light, thereby causing the transmitted red light to be incident on the dichroic mirror 175. As a result, the dichroic mirror 173 multiplexes the red light and the green light guided on the same optical axis, and causes multiplexed light to be incident on the dichroic mirror 175. Moreover, the dichroic mirror 175 reflects the blue light emitted from the blue light source 120B, thereby causing the reflected blue light to emit from the multiplexing module 170, and transmits the red light and the green light incident from a direction orthogonal to an incident direction of the blue light, thereby causing the transmitted red light and green light to emit from the multiplexing module 170. As a result, the multiplexing module 170 can multiplex and emit the red light, the green light, and the blue light guided on the same optical axis. The light emitted from the multiplexing module 170 is guided to, for example, the second collimating optical system 121 and the like.

The drive control unit 1021 controls driving of each of the red light source cooling unit 140R, the green light source cooling unit 140G, and the blue light source cooling unit 140B on the basis of a measured temperature and a target temperature of each of the light sources 120. Furthermore, the drive control unit 1021 controls driving of each of the red light source 120R, the green light source 120G, and the blue light source 120B on the basis of the amount of light detected by the light detection unit 160 and a target amount of light of each of the light sources 120.

Figure 3:
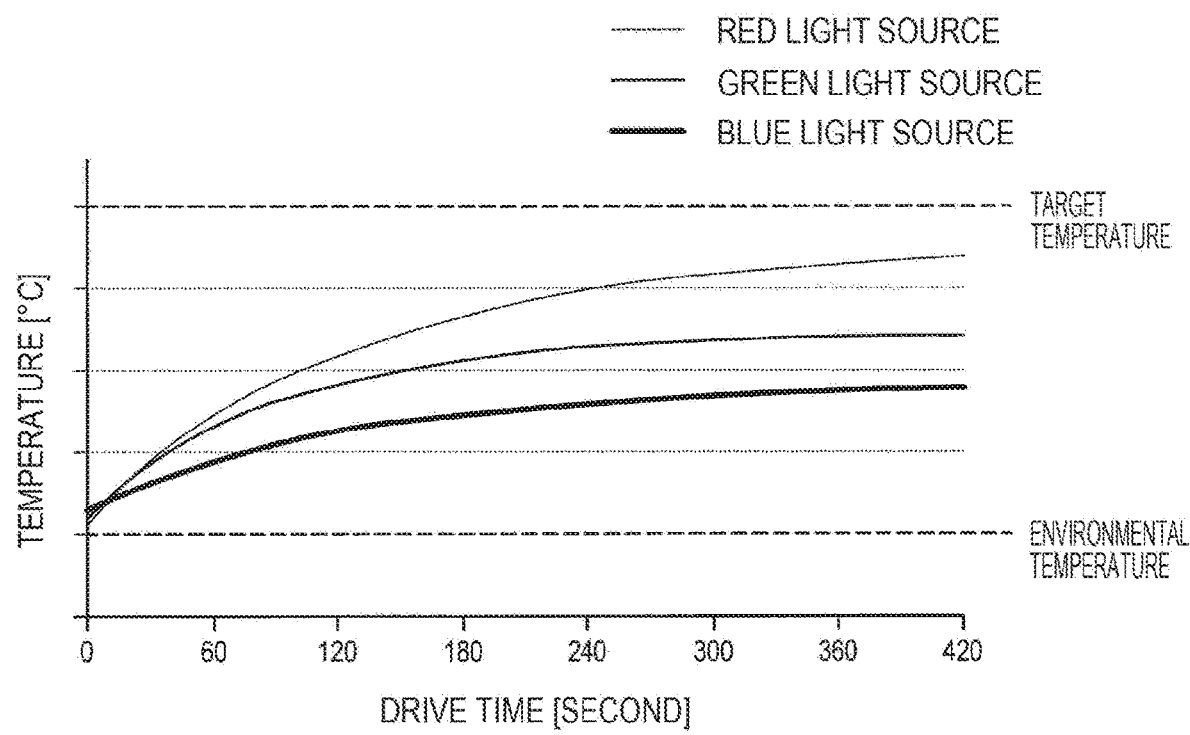
FIG. 3 is a graph illustrating temperature rises accompanying driving of light sources.
Figure 4:
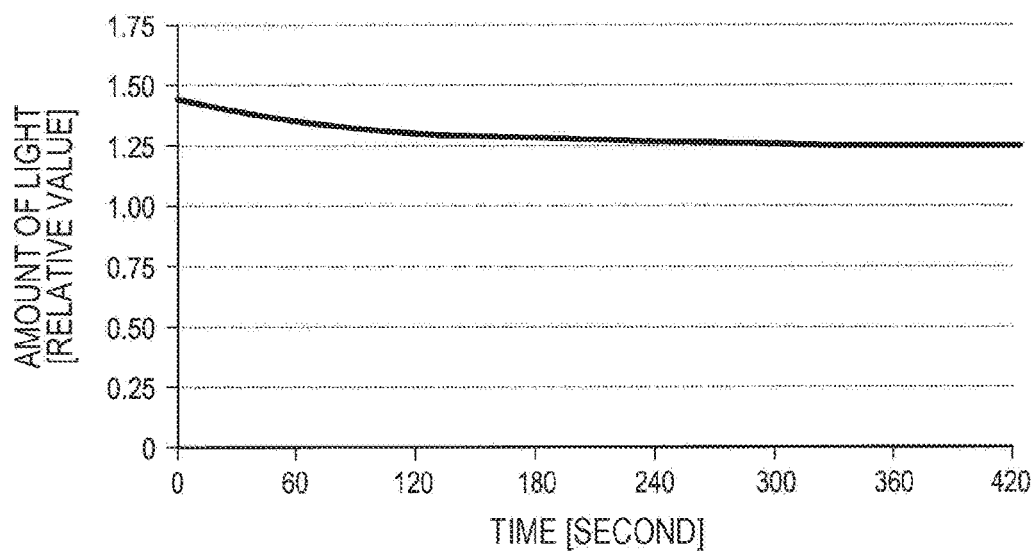
FIG. 4 is a graph illustrating a change in an amount of light of light emitted from the light source in a case where temperatures of the light sources rise in accordance with a drive time.

Here, the control by the drive control unit 1021 will be described more specifically with reference to FIGS. 3 to 5. FIG. 3 is a graph illustrating the temperature rises accompanying the driving of the light sources 120, and FIG. 4 is a graph illustrating a change in the amount of light of multiplexed light in which emitted lights from the respective light sources 120 are multiplexed in a case where the temperatures of the light sources 120 rise in accordance with a drive time as illustrated in FIG. 3.

In the illumination device according to the present embodiment, to stabilize the amounts of light emitted from the red light source 120R, the green light source 120G, and the blue light source 120B, it is sufficient that the temperature of the light source 120 is kept constant at the target temperature, for example. Here, the target temperature is a temperature at which heat generation by the driving of the light source 120 and cooling by the cooling unit 140 can be balanced, and a temperature suitable for light emission of the light source 120.

In the illumination device according to the present embodiment, the heating unit is not provided that heats the light source 120, and only the cooling unit 140 is provided that cools the light source 120. Therefore, in a case where the temperature of the light source 120 is higher than the target temperature, control can be performed to cause the temperature of the light source 120 to be the target temperature by cooling of the light source 120 by the cooling unit 140.

On the other hand, as illustrated in FIG. 3, in a case where the environmental temperature of the space where the illumination device is installed is lower than or equal to the target temperature, the temperature of each of the light sources 120 is almost the same as the environmental temperature immediately after the start of driving, so that the drive control unit 1021 cannot actively perform control to cause the temperature of the light source 120 to be the target temperature. On the other hand, the temperature of each of the light sources 120 rises with the heat generation caused by the driving as the drive time becomes longer. Furthermore, in the laser light source, as the temperature of the laser light source rises, the amount of light decreases of the light emitted. Therefore, in a case where the temperature of each of the light sources 120 rises as illustrated in FIG. 3, the amount of light of the illumination light in which the lights emitted from the light sources 120 are multiplexed gradually decreases as illustrated in FIG. 4.

Furthermore, in the light source 120, a calorific value varies for each of the light sources corresponding to respective colors, so that a rising speed varies of the temperature of the laser light source as illustrated in FIG. 3. Therefore, in the illumination light in which the lights emitted from the light sources 120 are multiplexed, even in a case where the amount of light does not fluctuate, a ratio of amounts of light fluctuates of the lights emitted from the respective light sources 120 depending on the drive time. In such a case, there is a possibility that the illumination light does not become a desired white light but becomes a light with a color.

Thus, in the first control example, in a case where the measured temperature of each of the light sources 120 is lower than or equal to the target temperature, the drive control unit 1021 controls the current applied to the light source 120 so that the amount of light of the light source 120 becomes constant.

Specifically, in a case where the measured temperature of the light source 120 is lower than or equal to the target temperature, there is a possibility that it takes time until the temperature of the light source 120 reaches the target temperature by the heat generation of driving, or the temperature of the light source 120 does not reach the target temperature, so that the drive control unit 1021 preferentially executes light amount control of the light source 120 based on the amount of light detected by the light detection unit 160. On the other hand, in a case where the measured temperature of the light source 120 is higher than the target temperature, control can be actively performed to cause the temperature of the light source 120 to be the target temperature by cooling by the cooling unit 140, so that the drive control unit 1021 preferentially executes the temperature control by the cooling unit 140.

Here, with reference to FIG. 5, a specific operation flow will be described of the above-described first control example. FIG. 5 is a flowchart illustrating the flow of the operation of the first control example.

Figure 5:
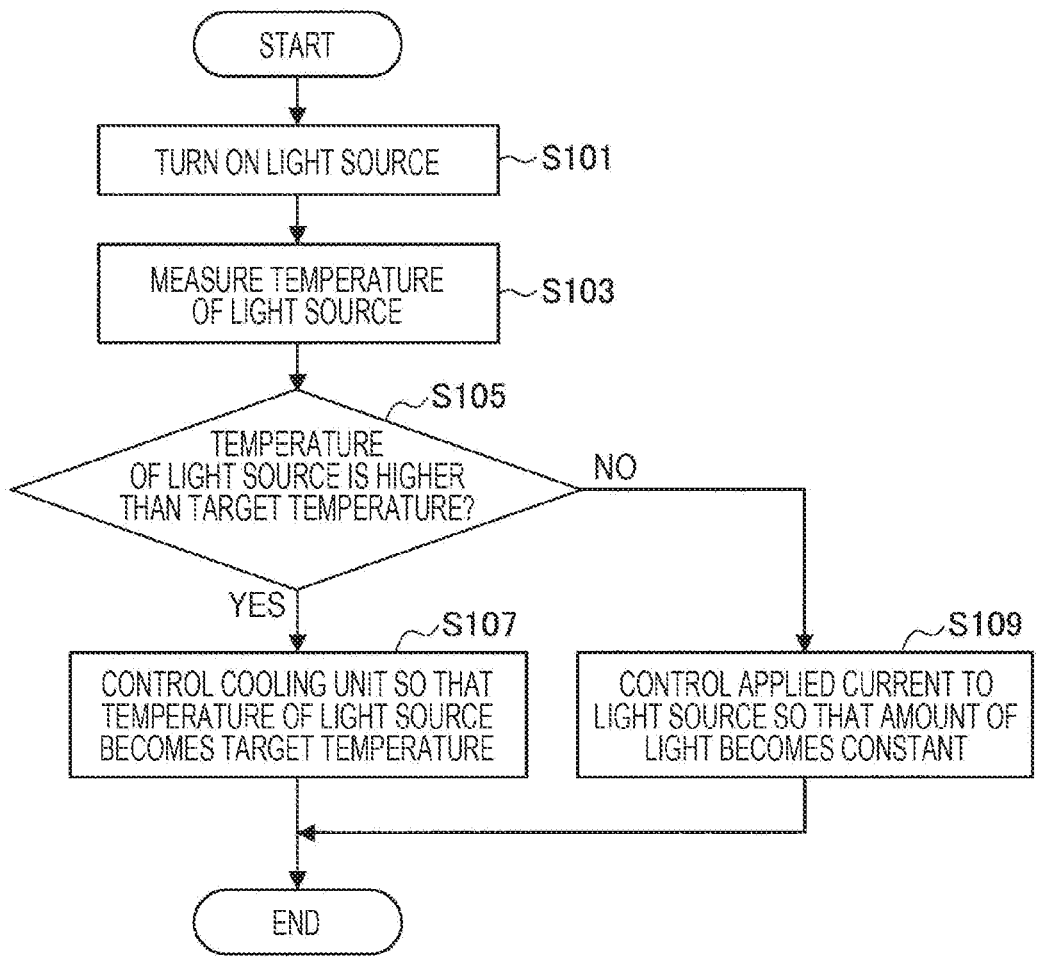
FIG. 5 is a flowchart illustrating a flow of operation of a first control example.

As illustrated in FIG. 5, first, each of the light sources 120 is turned on, whereby driving is started of the light sources 120 (S101). Next, the temperature of each of the light sources 120 is measured (S103), and it is determined whether or not the measured temperature of each of the light sources 120 is higher than the target temperature (S105). In a case where the measured temperature of each of the light sources 120 is higher than the target temperature (S105/Yes), the drive control unit 1021 controls the cooling unit 140 that cools the light source 120 so that the temperature of each of the light sources 120 becomes the target temperature (S107).

On the other hand, in a case where the measured temperature of each of the light sources 120 is lower than or equal to the target temperature (S105/No), the drive control unit 1021 controls an amount of current applied to the light source 120 so that the amount of light of each of the light sources 120 becomes constant (S109). The drive control unit 1021 controls the applied current to the light source 120, thereby being able to keep the amount of light of the light source 120 constant even in a case where control is not performed to cause the temperature of the light source 120 to be constant.

A comparison between the measured temperature of the light source 120 and the target temperature may be performed for each light source 120, and the drive control unit 1021 may make a different determination for each light source 120. For example, in a case where the measured temperature of the red light source 120R is higher than the target temperature and the measured temperatures of the green light source 120G and the blue light source 120B are lower than or equal to the respective target temperatures, the drive control unit 1021 may perform control to cause the temperature of the red light source 120R to be the target temperature, or may perform control to cause the amounts of light of the green light source 120G and the blue light source 120B to be constant.

Note that, controlling the current applied to the light source 120 so that the amount of light of the light source 120 becomes constant on the basis of the amount of light detected by the light detection unit 160, is also referred to constant output control (auto power control: APC), for example. On the other hand, driving the light source 120 so that the current applied to the light source 120 becomes constant, is also referred to as constant current control (auto current control: ACC), for example.

Figure 6:
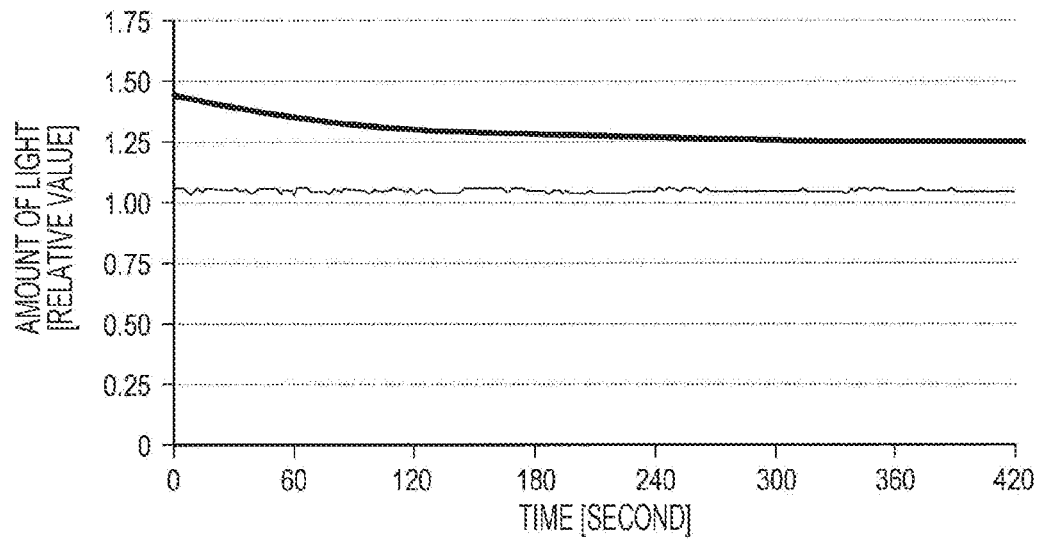
FIG. 6 is a graph illustrating a change in the amount of light of light emitted from light sources controlled by APC or ACC in a case where the temperatures of the light sources rise in accordance with the drive time.

Here, with reference to FIG. 6, a change in the amount of light of the light source 120 will be described in each of the constant output control (APC) and the constant current control (ACC). FIG. 6 is a graph illustrating a change in the amount of light of multiplexed light in which emitted lights from the respective light sources 120 controlled by APC or ACC are multiplexed in a case where the temperatures of the light sources 120 rise in accordance with the drive time as illustrated in FIG. 3.

As illustrated in FIG. 6, in the constant current control (ACC), the temperature of the light source 120 rises as the drive time becomes longer, so that the amount of light of the multiplexed light emitted is reduced due to the fluctuation of the light output characteristic of the light source 120. On the other hand, in the constant output control (APC), even in a case where the temperature of the light source 120 rises with the drive time, the amount of light can be kept constant of the multiplexed light emitted.

According to the first control method, even when not including the heating unit for each light source 120, the illumination device can keep the amount of light constant of the light emitted from each of the light sources 120 by performing switching between the cooling control and the constant output control on the basis of the comparison between the measured temperature of each of the light sources 120 and the target temperature.

Note that, in a case where the measured temperature of each of the light sources 120 exceeds the target temperature, performing constant output control on each of the light sources 120 increases power consumption. Therefore, according to the first control method that performs switching between the cooling control and the constant current control for each of the light sources 120 on the basis of the comparison between the measured temperature of each of the light sources 120 and the target temperature, the power consumption can be reduced.

(2.2. Second Control Method)

Figure 7:
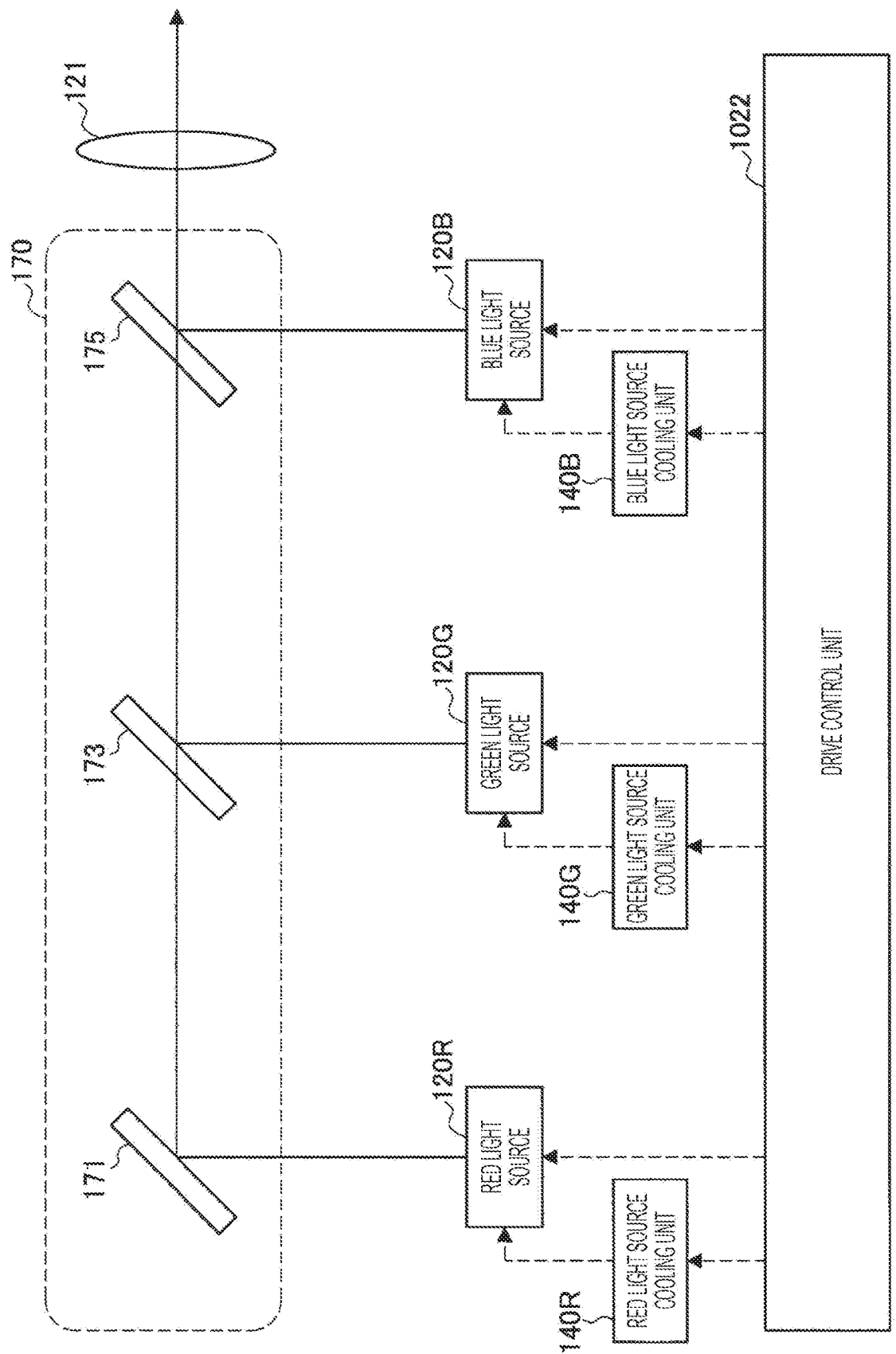
FIG. 7 is a block diagram illustrating each component of an illumination device according to a second control method.
Figure 8:
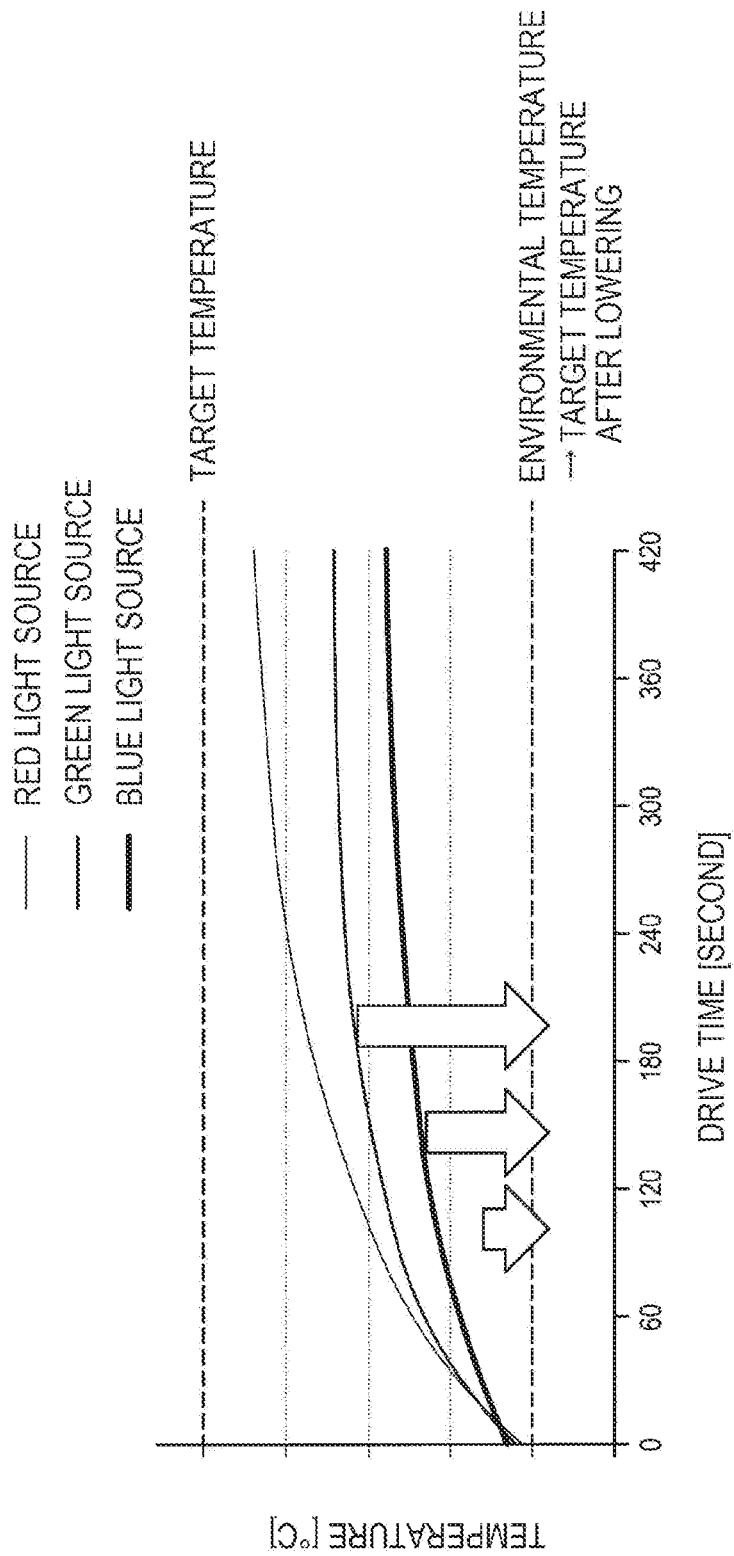
FIG. 8 is a graph illustrating the temperature rises accompanying the driving of the light sources.

Next, with reference to FIGS. 7 to 9, a second control method of the illumination device will be described. FIG. 7 is a block diagram illustrating each component of an illumination device according to the second control method.

In the illumination device according to the second control method, similarly to the illumination device according to the first control method, each laser light source includes the cooling unit, but does not include the heating unit. Therefore, in the illumination device according to the second control method, similarly to the illumination device according to the first control method, the number of parts can be reduced of the control circuit that controls the heating unit. However, due to the fact that each laser light source does not include the heating unit, in the case where the temperature of each laser light source of the illumination device is lower than the target temperature for stabilization, the temperature of each laser light source may fluctuate. In the second control method, a control method is provided for keeping the temperature of the illumination device constant even in such a case.

As illustrated in FIG. 7, the configuration of the illumination device according to the second control method is substantially similar to that of the illumination device according to the first control method except that the light sampler 161 and the light detection unit 160 are not included, so that the explanation here will be omitted. However, it goes without saying that the illumination device according to the second control method may include the light sampler 161 and the light detection unit 160.

Here, control by a drive control unit 1022 will be described more specifically with reference to FIG. 8. FIG. 8 is a graph illustrating the temperature rises accompanying the driving of the light sources 120.

In the illumination device according to the present embodiment, to stabilize the amounts of light emitted from the red light source 120R, the green light source 120G, and the blue light source 120B, it is sufficient that the temperature of the light source 120 is kept constant at the target temperature, for example. However, as illustrated in FIG. 8, in a case where the environmental temperature of the space where the illumination device is installed is lower than or equal to the target temperature, the temperature of each of the light sources 120 is almost the same as the environmental temperature immediately after the start of driving, it takes time for the temperature of each of the light sources 120 to reach the target temperature by heat generation by driving.

Thus, in the second control example, in a case where the measured temperature of the environment in which the illumination device is installed is lower than the target temperature, the drive control unit 1022 lowers the target temperature, thereby performing control so that the temperature control of the light source 120 can be performed by the cooling unit 140. Note that, in a case where the measured temperature of the environment in which the illumination device is installed is higher than or equal to the target temperature, the drive control unit 1022 controls the cooling unit 140 that cools the light source 120 so that the temperature of the light source 120 becomes the initial target temperature.

Specifically, in a case where the measured temperature of the environment is lower than the target temperature, it is assumed that the temperature of each of the light sources 120 is lower than the target temperature similarly. At this time, it may take a very long time to cause the temperature of the light source 120 to reach the target temperature by heat generation of driving. Therefore, as illustrated in FIG. 8, the drive control unit 1022 lowers the target temperature to the vicinity of the measured temperature of the environment, thereby making it possible to perform control to cause the temperature of the light source 120 to be the target temperature by cooling by the cooling unit 140 and heat generation of driving.

The drive control unit 1022 may set the target temperature after the lowering on the basis of the measured temperature of the environment. For example, as illustrated in FIG. 8, the drive control unit 1022 may set the measured temperature of the environment as the target temperature after the lowering. Furthermore, the drive control unit 1022 may set a temperature higher by a predetermined value from the measured temperature of the environment, as the target temperature after the lowering. The predetermined value may be determined according to a temperature rise curve estimated from an electro-optical conversion efficiency of the light source 120 and a required specification of the time until the output amount of light becomes stable. Furthermore, the drive control unit 1022 may set a temperature closest to the measured temperature of the environment among a plurality of temperatures set in advance at predetermined intervals, as the target temperature after the lowering.

However, in a case where the measured temperature of the environment is lower than the target temperature and the target temperature is lowered, the drive control unit 1022 does not lower the target temperature below the measured temperature of the environment. This is because, since the light source 120 generates heat by driving, the drive control unit 1022 can perform control to cause the temperature of the light source 120 to be the target temperature after the lowering, by the cooling unit 140, if the target temperature is lowered to at least the measured temperature of the environment. For example, in a case where the target temperature is lowered to a temperature lower than the measured temperature of the environment, the drive control unit 1022 excessively performs cooling by the cooling unit 140, so that power consumption is increased.

Note that, in a case where the drive control unit 1022 lowers the target temperature, the light output characteristic of the light source 120 at the target temperature after the lowering fluctuates from the light output characteristic of the light source 120 at the initial target temperature. In such a case, since the light output characteristic of each of the light sources 120 fluctuates, there is a possibility that the color is changed of the illumination light in which the lights emitted from the light sources 120 are multiplexed.

Therefore, the drive control unit 1022 may store the light output characteristic of the light source 120 at each temperature in advance, and control the current applied to the light source 120 on the basis of the light output characteristic of the light source 120 at the target temperature after the lowering. Furthermore, in a case where the plurality of temperatures at predetermined intervals is set as target temperatures after the lowering, the drive control unit 1022 may store in advance the light output characteristics of the light source 120 at the plurality of temperatures set as the target temperatures after the lowering, and control the current applied to the light source 120 on the basis of the light output characteristics.

Furthermore, in a case where the illumination device includes the light sampler 161 and the light detection unit 160, the drive control unit 1022 may control the current applied to the light source 120 so that a desired amount of light is obtained on the basis of the amount of light of the light of the light source 120 detected by the light detection unit 160.

Here, with reference to FIG. 9, a specific operation flow will be described of the above-described second control example. FIG. 9 is a flowchart illustrating the flow of the operation of the second control example.

Figure 9:
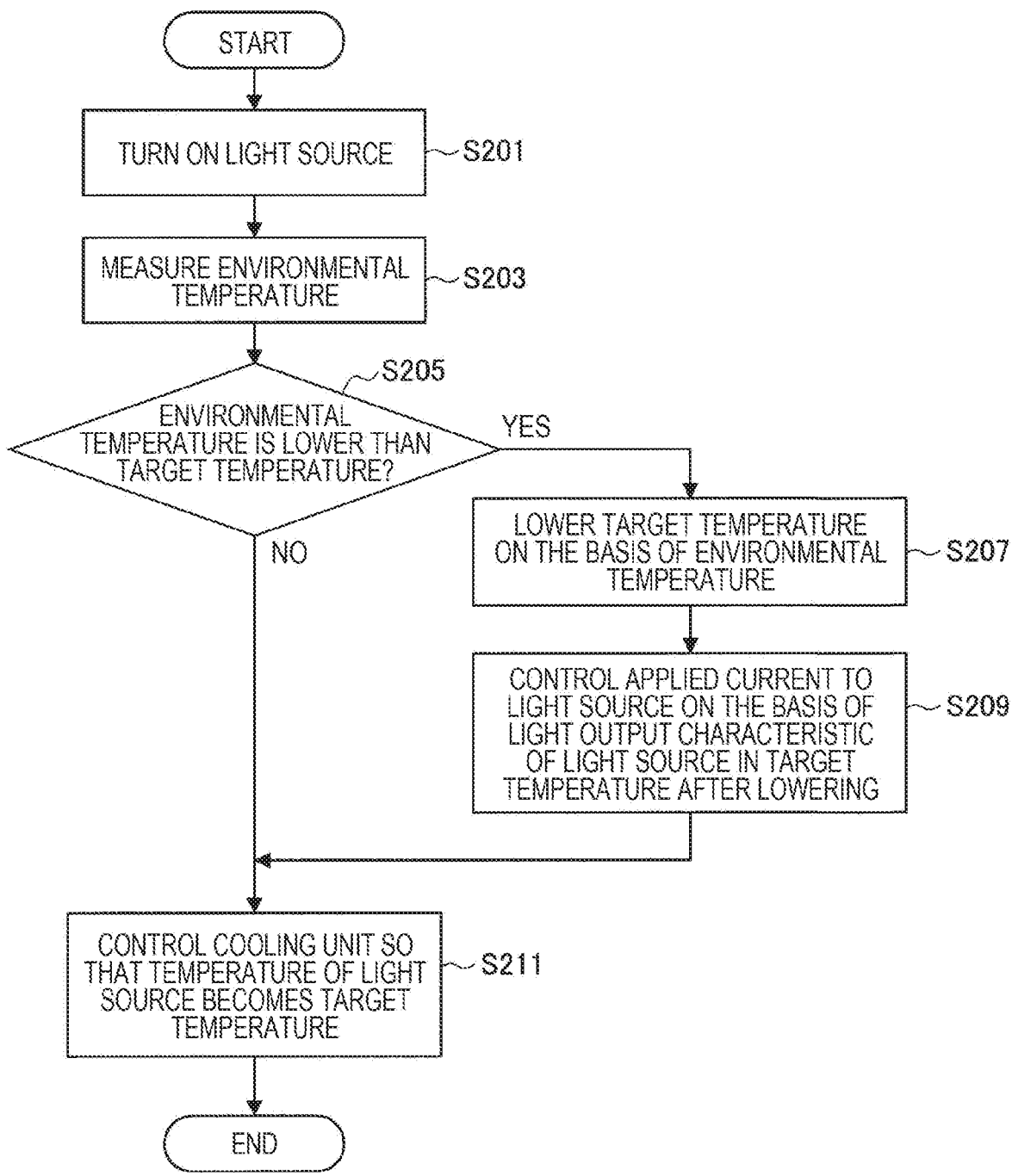
FIG. 9 is a flowchart illustrating a flow of operation of a second control example.

As illustrated in FIG. 9, first, each of the light sources 120 is turned on, whereby driving is started of each of the light sources 120 (S201). Next, the environmental temperature is measured at which the illumination device is installed (S203). Subsequently, it is determined whether or not the measured environmental temperature is lower than the target temperature (S205). In a case where the measured environmental temperature is lower than the target temperature (S205/Yes), the drive control unit 1022 lowers the target temperature on the basis of the measured environmental temperature (S207).

As a result, it is assumed that the temperature of the light source 120 is higher than or substantially equal to the target temperature after the lowering, so that the drive control unit 1022 can perform control to cause the temperature of the light source 120 to be the target temperature after the lowering, by the cooling unit 140. Furthermore, the drive control unit 1022 controls the current applied to the light source 120 on the basis of the light output characteristic of the light source 120 at the target temperature after the lowering (S209), and controls cooling by the cooling unit 140 so that the temperature of the light source 120 becomes the target temperature after the lowering (S211).

On the other hand, in a case where the measured environmental temperature is higher than or equal to the target temperature (S205/No), the drive control unit 1022 controls cooling of the light source 120 by the cooling unit 140 so that the temperature of the light source 120 becomes the target temperature (S211). At this time, it is assumed that the temperature of the light source 120 is higher than or substantially equal to the target temperature, so that the drive control unit 1022 can perform control to cause the temperature of the light source 120 to be the target temperature by the cooling unit 140.

According to the second control method, even when not including the heating unit for each light source 120, the illumination device can keep the temperature of each of the light sources 120 constant by lowering the target temperature on the basis of the comparison between the measured environmental temperature and the target temperature. As a result, the illumination device can keep the amount of light of the light emitted from the light source 120 constant by keeping the temperature of each of the light sources 120 constant.

(2.3. Third Control Method)

Figure 10:
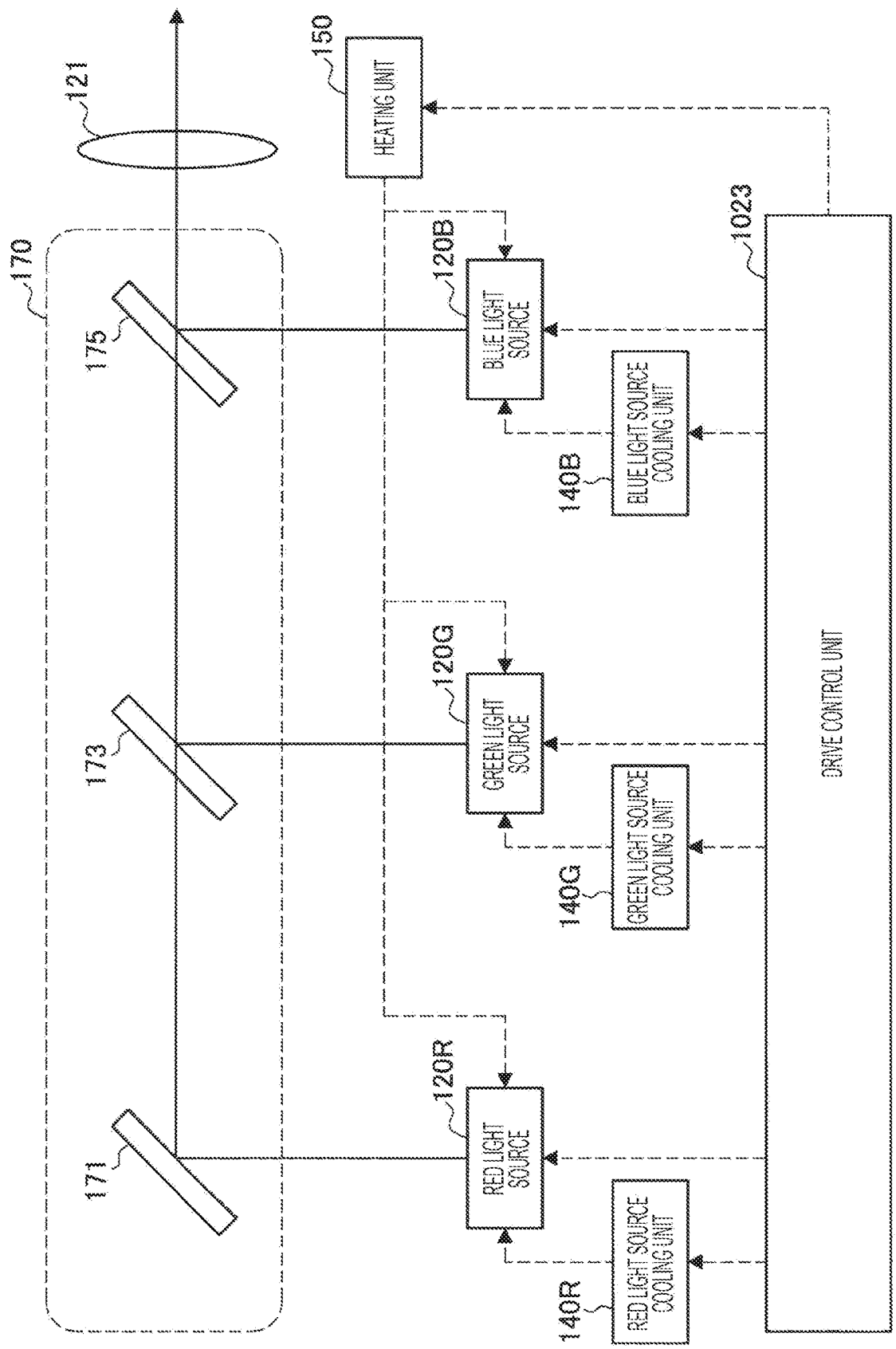
FIG. 10 is a block diagram illustrating each component of an illumination device according to a third control method.

Next, with reference to FIGS. 10 and 11, a third control method of the illumination device will be described. FIG. 10 is a block diagram illustrating each component of an illumination device according to the third control method.

In the illumination device according to the third control method, similarly to the illumination device according to the first control method, each laser light source includes a cooling unit, but does not include a heating unit that is individually controlled. However, in the illumination device according to the third control method, a heating unit is provided that collectively heats each laser light source. Therefore, in the illumination device according to the third control method, a control circuit of the heating unit individually provided for each laser light source can be omitted and aggregated in a control circuit of the heating unit that collectively heats each laser light source. Therefore, according to the third control method, the number of parts of the control circuit can be reduced, in the illumination device.

As illustrated in FIG. 10, the configuration of the illumination device according to the third control method is substantially similar to that of the illumination device according to the second control method except that a heating unit 150 is provided that collectively heats each of the light sources 120. Therefore, the explanation here will be omitted for the configuration substantially similar to that of the illumination device according to the second control method.

Only one heating unit 150 is provided in the illumination device, and the heating unit 150 collectively heats the red light source 120R, the green light source 120G, and the blue light source 120B. The heating unit 150 may be a thermoelectric element, for example, a resistor, a Peltier element, or the like. However, in a case where the Peltier element is used for the heating unit 150, the Peltier element is configured to execute only the function of heating the light source 120. Specifically, in the Peltier element constituting the heating unit 150, only a circuit is provided for supplying a current in a direction to heat the light source 120, and a circuit is not provided for supplying a current in a direction to cool the light source 120.

Note that, the heating unit 150 may be constituted by a plurality of resistors or a plurality of Peltier elements. Specifically, the heating unit 150 may be constituted by a plurality of resistors connected in series, and each of the plurality of resistors may be provided in the vicinity of each of the light sources 120. Even in such a case, the plurality of resistors constituting the heating unit 150 is not provided with a control circuit that individually controls the plurality of resistors, and heating or non-heating is controlled by the same control circuit, so that the number of parts of the control circuit can be reduced.

In the third control example, in a case where a temperature of any of the light sources 120 is lower than the target temperature, a drive control unit 1023 drives the heating unit 150, thereby controlling the temperature of the light source 120 so that all the temperatures of the light sources 120 become higher than or equal to the respective target temperatures. As a result, the drive control unit 1023 can raise the temperature of the light source 120 by collectively heating each of the light sources 120, so that the temperature of the light source 120 can be controlled by the cooling unit 140. Note that, in a case where all the temperatures of the light sources 120 are higher than or equal to the respective target temperatures, the drive control unit 1023 controls the cooling unit 140 so that the temperature of each of the light sources 120 becomes the target temperature.

In such a case, the drive control unit 1023 can cause the light source 120 to emit light at the initially set target temperature, so that the light source 120 can be caused to emit light more efficiently. Furthermore, since the oscillation wavelength of the laser light source may be shifted depending on the temperature, the drive control unit 1023 causes the light source 120 to emit light at the initially set target temperature, whereby emitted light of a desired wavelength spectrum can be obtained from the light source 120.

Here, with reference to FIG. 11, a specific operation flow will be described of the above-described third control example. FIG. 11 is a flowchart illustrating the flow of the operation of the third control example.

As illustrated in FIG. 11, first, each of the light sources 120 is turned on, whereby driving is started of each of the light sources 120 (S301). Next, the temperature of each of the light sources 120 is measured (S303). Subsequently, it is determined whether or not the measured temperatures of all the light sources 120 are higher than or equal to the respective target temperatures (S305). In a case where the measured temperature of any of the light sources 120 is lower than the target temperature (S305/No), the drive control unit 1023 causes the heating unit 150 to heat each of the light sources 120 until the measured temperatures of all the light sources 120 becomes higher than or equal to the respective target temperatures (S307). As a result, the temperatures of all the light sources 120 can be made higher than or equal to the respective target temperatures, so that the drive control unit 1023 can perform control to cause the temperature of each of the light sources 120 to be the target temperature by the cooling unit 140. Thereafter, the drive control unit 1023 controls cooling by the cooling unit 140 so that the temperature of each of the light sources 120 becomes the target temperature (S309).

On the other hand, in a case where the measured temperatures of all the light sources 120 are higher than or equal to the respective target temperatures (S305/No), the drive control unit 1023 controls cooling by the cooling unit 140 so that the temperature of each of the light sources 120 becomes the target temperature (S309). At this time, since the temperatures of all the light sources 120 are higher than or equal to the respective target temperatures, the drive control unit 1023 can perform control to cause the temperature of each of the light sources 120 to be the target temperature by the cooling unit 140.

According to the third control method, in the illumination device, the heating unit individually provided for each light source 120 can be omitted by aggregation to the heating unit 150 that collectively heats all the light sources 120. As a result, in the illumination device, the number of parts can be reduced of the control circuit that controls the individual heating units.

Furthermore, according to the third control method, each of the light sources 120 can be caused to emit light at the initially set target temperature, so that the emitted light of the desired wavelength spectrum can be obtained from the light source 120 more efficiently.

3. Conclusion

As described above, with the illumination device according to the embodiment of the present disclosure, the circuit is omitted that controls the individual heating for each of the plurality of light sources, whereby the control circuit can be simplified, so that the number of parts of the control circuit can be reduced. As a result, with the reduction in the number of parts of the circuit, the manufacturing cost of the illumination device can be reduced, and with the simplification of the configuration, the reliability of the illumination device can be improved.

In the above, the preferred embodiments of the present disclosure have been described in detail with reference to the accompanying drawings; however, the technical scope of the present disclosure is not limited to such examples. It is obvious that persons having ordinary knowledge in the technical field of the present disclosure can conceive various modification examples or correction examples within the scope of the technical idea described in the claims, and it is understood that the modification examples or correction examples also belong to the technical scope of the present disclosure.

Furthermore, the effects described in the present specification are merely illustrative or exemplary and not restrictive. That is, the technology according to the present disclosure can exhibit other effects obvious to those skilled in the art from the description of the present specification together with the above-described effects or in place of the above effects.

Note that, the following configurations also belong to the technical scope of the present disclosure.

(1)

An illumination device including:

a plurality of light sources;

a plurality of cooling units respectively provided for the light sources and respectively cooling the light sources; and a drive control unit that performs switching of control with respect to each of the light sources on the basis of a comparison between a target temperature of each of the light sources and a measured temperature of each of the light sources or an environment.

(2)

The illumination device according to (1), further including a plurality of light detection units respectively provided for the light sources and respectively detecting amounts of light of the light sources, in which the drive control unit controls the cooling units to cause a temperature of each of the light sources to be the target temperature in a case where the measured temperature of each of the light sources is higher than the target temperature, and performs control to cause an amount of light of each of the light sources to be constant on the basis of the amount of light of each of the light sources detected by a corresponding one of the light detection units in a case where the measured temperature of each of the light sources is lower than or equal to the target temperature.

(3)

The illumination device according to (1), in which the drive control unit lowers the target temperature in a case where the measured temperature of the environment is lower than the target temperature.

(4)

The illumination device according to (3), in which a target temperature after lowering by the drive control unit is higher than or equal to the measured temperature of the environment.

(5)

The illumination device according to (4), in which the drive control unit determines the target temperature after the lowering on the basis of the measured temperature of the environment.

(6)

The illumination device according to any one of (3) to (5), in which the drive control unit controls a current applied to each of the light sources on the basis of a light output characteristic of each of the light sources at the target temperature after the lowering.

(7)

The illumination device according to any one of (3) to (5), further including a plurality of light detection units respectively provided for the light sources and respectively detecting amounts of light of the light sources, in which the drive control unit performs control to cause an amount of light of each of the light sources to be constant on the basis of the amount of light of each of the light sources detected by a corresponding one of the light detection units.

(8)

The illumination device according to any one of (1) to (7), further including a heating unit that collectively heats the plurality of light sources, in which the drive control unit controls the heating unit to cause each of temperatures of the plurality of light sources to be higher than or equal to the target temperature in a case where a measured temperature of any of the light sources is lower than the target temperature.

(9)

The illumination device according to any one of (1) to (8), in which the plurality of light sources is a plurality of laser light sources respectively having different wavelength spectra of emitted light.

(10)

The illumination device according to any one of (1) to (9), in which the illumination device is not provided with individual heating units respectively controlled for the plurality of light sources.

(11)

A control device including a drive control unit that performs switching of control with respect to each of a plurality of light sources, the control including at least control of a plurality of cooling units respectively provided for the light sources, on the basis of a comparison between a target temperature of each of the light sources and a measured temperature of each of the light sources or an environment.

(12)

A control method including performing switching of control with respect to each of a plurality of light sources, the control including at least control of a plurality of cooling units respectively provided for the light sources, on the basis of a comparison between a target temperature of each of the light sources and a measured temperature of each of the light sources or an environment.

REFERENCE SIGNS LIST

1 Observation device
10 Light source unit
20 Endoscope unit
30 Information processing device
31 Display device
32 Input device
40 Observation target
100 Control unit
120 Light source
140 Cooling unit
150 Heating unit
160 Light detection unit
161 Light sampler
170 Multiplexing module
171 Mirror
173, 175 Dichroic mirror
1021, 1022, 1023 Drive control unit

The invention claimed is:

1. An illumination device, comprising:
a plurality of light sources configured to emit light;
a plurality of cooling units that corresponds to the plurality of light sources, wherein each cooling unit of the plurality of cooling units is configured to cool a respective light source of the plurality of light sources;
a plurality of light detection units corresponding to the plurality of light sources, wherein each light detection unit of the plurality of light detection units is configured to detect an amount of light emitted from the respective light source of the plurality of light sources; and
a drive control unit configured to control drive of each light source of the plurality of light sources such that the amount of light emitted from each light source of the plurality of light sources is constant, in a case where a measured temperature of each light source of the plurality of light sources and a measured temperature of an environment is lower than a target temperature of the respective light source of the plurality of light sources, wherein
the control of the drive of each light source of the plurality of light sources is based on the amount of light detected by a corresponding light detection unit of the plurality of light detection units, and
in the case where the measured temperature of each light source of the plurality of light sources and the measured temperature of the environment is lower than the target temperature, the measured temperature of each light source of the plurality of light sources reaches the target temperature based on heat generation by the drive of the respective light source of the plurality of light sources.

2. The illumination device according to claim 1, wherein the drive control unit is further configured to control the plurality of cooling units to cause a temperature of each light source of the plurality of light sources to reach the target temperature, wherein the control of the plurality of cooling units is based on the measured temperature of each light source of the plurality of light sources that is higher than the target temperature.

3. The illumination device according to claim 1, wherein the drive control unit is further configured to lower the target temperature in a case where the measured temperature of the environment is lower than the target temperature.

4. The illumination device according to claim 3, wherein the lowered target temperature is one of higher than or equal to the measured temperature of the environment.

5. The illumination device according to claim 4, wherein the drive control unit is further configured to determine the lowered target temperature based on the measured temperature of the environment.

6. The illumination device according to claim 3, wherein the drive control unit is further configured to control a current applied to each light source of the plurality of light sources based on a light output characteristic of the respective light source of the plurality of light sources at the lowered target temperature.

7. The illumination device according to claim 1, further comprising
a heating unit configured to collectively heat the plurality of light sources, wherein
the drive control unit is further configured to control the heating unit to control temperatures of the plurality of light sources to be one of higher than or equal to the target temperature in a case where the measured temperature of one of the plurality of light sources is lower than the target temperature.

8. The illumination device according to claim 1, wherein the plurality of light sources is a plurality of laser light sources respectively having different wavelength spectra of light emission.

9. The illumination device according to claim 1, further comprising a heating unit, wherein control unit is further configured to control the heating unit to collectively heat the plurality of light sources.

10. A control device, comprising:
a drive control unit configured to:
control drive of each light source of a plurality of light sources such that an amount of light emitted from each light source of the plurality of light sources is constant, in a case where a measured temperature of each light source of the plurality of light sources and a measured temperature of an environment is lower than a target temperature of a respective light source of the plurality of light sources, wherein
the control of the drive of each light source of the plurality of light sources is based on the amount of light detected by a corresponding light detection unit of a plurality of detection units, and
in the case where the measured temperature of each light source of the plurality of light sources and the measured temperature of the environment is lower than the target temperature, the measured temperature of each light source of the plurality of light sources reaches the target temperature based on heat generation by the drive of the respective light source of the plurality of light sources; and
control a plurality of cooling units corresponding to the plurality of light sources to cause the measured temperature of each light source of the plurality of light sources to reach the target temperature, wherein the control of the plurality of cooling units is based on the measured temperature of each light source of the plurality of light sources that is higher than the target temperature.

11. A control method, comprising:
controlling drive of each light source of a plurality of light sources such that an amount of light emitted from each light source of the plurality of light sources is constant, in a case where a measured temperature of each light source of the plurality of light sources and a measured temperature of an environment is lower than a target temperature of a respective light source of the plurality of light sources, wherein
the control of the drive of each light source of the plurality of light sources is based on the amount of light detected by a corresponding light detection unit of a plurality of detection units, and
in the case where the measured temperature of each light source of the plurality of light sources and the measured temperature of the environment is lower than the target temperature, the measured temperature of each light source of the plurality of light sources reaches the target temperature based on heat generation by the drive of the respective light source of the plurality of light sources; and
controlling a plurality of cooling units corresponding to the plurality of light sources to cause the measured temperature of each light source of the plurality of light sources to reach the target temperature, wherein the control of the plurality of cooling units is based on the measured temperature of each light source of the plurality of light sources that is higher than the target temperature.

\* \* \* \* \*